United States Patent [19]

Bashikirov

[11] Patent Number: 5,571,082

[45] Date of Patent: Nov. 5, 1996

[54] METHOD OF PRODUCING THERAPEUTIC EFFECT UPON AN ORGANISM TO REDUCE THE PATHOLOGIC LYMPHOCYTE POPULATION

[76] Inventor: Alexei B. Bashikirov, 12, Akademichesky prospekt, apt. 12, Puchkin, St. Petersburg, 189620, Russian Federation

[21] Appl. No.: 283,624

[22] Filed: Aug. 1, 1994

[30] Foreign Application Priority Data

Aug. 2, 1993 [RU] Russian Federation ............ 93038964

[51] Int. Cl.$^6$ ................................................. A61M 37/00
[52] U.S. Cl. ............................ 604/4; 604/52; 604/21; 604/28; 422/44
[58] Field of Search ...................... 604/4–6, 20, 28, 604/21, 27, 49–53; 422/44; 128/DIG. 3

[56] References Cited

U.S. PATENT DOCUMENTS

| | | | |
|---|---|---|---|
| 4,398,906 | 8/1983 | Edelson | 640/6 |
| 4,464,166 | 8/1984 | Edelson | 604/6 |
| 4,512,762 | 4/1985 | Spears | 604/53 |
| 4,563,170 | 1/1986 | Aigner | 604/27 |
| 4,612,007 | 9/1986 | Edelson . | |
| 4,613,322 | 9/1986 | Edelson . | |
| 4,708,715 | 11/1987 | Troutner | 604/6 |
| 4,838,852 | 6/1989 | Edelson | 604/4 |
| 5,030,200 | 7/1991 | Judy | 604/5 |

FOREIGN PATENT DOCUMENTS

PCT/GB88/00951 11/1988 WIPO .

*Primary Examiner*—Randall L. Green
*Assistant Examiner*—Chalin Smith
*Attorney, Agent, or Firm*—Beveridge, DeGrandi, Weilacher & Young, L.L.P.

[57] ABSTRACT

A method of producing a therapeutic effect upon a living organism endowed with a lymphatic system, comprising the steps of with drawing from said organism a biological fluid, wherein lymphocytes prevail as the cellular constituents, and introducing into said biological fluid a photo-active chemical agent soluble therein. The chemical agent has a specific affinity for the receptor sites in or on the fluid constituents, and is capable of being activated by ultraviolet radiation, and, when activated by said ultraviolet radiation, of forming photo-adducts with receptor sites of the fluid constituents, thereby ensuring chemical linkage between said photo-active chemical agent and said receptor sites. The method further includes irradiating the biological fluid, with the photo-active chemical agent introduced thereinto, by ultraviolet light, and introducing said biological fluid after said irradiation back into said lymphatic system. Irradiation may be effected endolymphatically.

14 Claims, No Drawings

METHOD OF PRODUCING THERAPEUTIC EFFECT UPON AN ORGANISM TO REDUCE THE PATHOLOGIC LYMPHOCYTE POPULATION

FIELD OF THE INVENTION

The present invention is in the field of immunology, relating more specifically to methods of modifying the immune system of a mammal for suppressing the functioning population of immunocompetent cells (lymphocytes) the invention can be used for therapy of human and animal diseases, including certain oncological diseases (leukoses, cutaneous T-cell lymphomas, etc.), and auto-immune diseases (hepatitis B, rheumatoid arthritis, etc.).

BACKGROUND OF THE INVENTION

For treatment of diseases associated with functional disturbances in the immune system, there are known methods operating by suppression of lymphocytes.

There is known a method for producing a therapeutic effect upon the organism, disclosed in PCT/GB88/00951, which comprises withdrawal of lymph from the thoracic duct of a patient, irradiating the lymph withdrawn by ultraviolet light, and returning the irradiated lymph to the lymphatic system of the patient.

When exposed to ultraviolet radiation, lymphocytes undergo direct degradation leading, in the final analysis, to their death. Considering the fact that most of the lymphocytes are pathologic cells, it is pathologic lymphocytes that are mainly destroyed. Thence the therapeutic effect.

However the lymphocytes so irradiated are not sufficiently immunogenic. That is to say, when these are introduced into the lymphatic system, the healthy immunocompetent cells of the lymphoid tissue are not capable of effecting a reaction when in contact with irradiated lymphocytes, such that would originate an immune response aimed at degradation or suppression of the functional and metabolic activities of such pathologic cells by the organism itself.

To achieve effective suppression of the pathologic lymphocytes by the organism itself, there is added to the biological fluid enriched with lymphocytes a photo-active chemical agent which has a specific affinity for the receptor sites in or on the constituents of said biological fluid, which is activated by ultraviolet radiation, and which is capable, when activated by said ultraviolet radiation, of forming photo-adducts with receptor sites of the constituents of said biological fluid, thereby assuring chemical linkage between said photo-active chemical agent and said receptor sites.

Added to the biological fluid enriched with lymphocytes, the photo-active chemical agent is adsorbed on the cell membranes, cell nucleus membranes, and cell and nucleus contents, as well as on the constituents of the intracellular fluid. Affected by ultraviolet radiation, the photo-active chemical agent passes into an active state and becomes highly reactive. In such a state, some photo-active chemical agents, e.g. of the furocoumarin class, form covalent linkages between the pyrimidines of the complementary DNA chains in a cell's nucleus, thereby preventing the possibility of divergence of DNA chains when the cell divided. In this manner, lymphocyte proliferation is prevented.

At the same time, affected by ultraviolet radiation, the photo-active chemical agent adsorbed at the receptor sites in or on the biological fluid constituents will either considerably intensify the photochemical reactions occurring under the effect of ultraviolet radiation (oxygen-dependent free radical reactions of cellular membrane lipids), which leads to changes in the receptor field of the membranes and their antigenic determinants, or increase the agent's specific effect level (when this agent is a carrier-photo-active group complex, and the carrier is a biologically active moiety having a specific suppressive effect upon immunocompetent cells, e.g. antibodies, cortisone, etc.). Thus, in said processes, the therapeutic effect is achieved by directly destroying or suppressing the functional and metabolic activities of the treated cells, which leads to a decrease in the cell concentration in the treated fluid, while, on the other hand, introduction into the organism of treated cells and fragments thereof with heavily changed antigenic structures (this being due to the formation-owing to the effect of ultraviolet irradiation-of photo-adducts comprising cellular components and photo-active chemical agent molecules) leads to the formation of an immune response by the organism, which is purposed to suppress the population of pathologic cells. Since the concentration of pathologic cells essentially exceeds that of healthy ones and also because it is in these that metabolic processes are most active, the photochemical effect is primarily upon pathologic cells, and it is these cells that are capable of causing-following the formation of covalent bonded stable photo-adducts and introduction of these into the organism-a systemic immune response aimed thereagainst.

U.S. Pat. No. 4,613,322 discloses a method for producing therapeutic effect upon the organism, comprising withdrawal of blood from a patient, centrifuging the blood drawn to separate red blood cells and most of the plasma, and obtaining a fraction, in which lymphocytes make the predominant cellular constituent. Said lymphocyte-rich fraction is then exposed to irradiation by ultraviolet light in the presence of a dissolved photo-active chemical agent which is introduced into the organism of the patient 2 hours before blood withdrawal. The blood fraction so irradiated is then returned to the blood supply system of the patient.

When said irradiated blood fraction is returned to the blood channel, the immunogenic photo-adducts formed by exposure to ultraviolet radiation with the participation of constituents of the treated fluid and molecules of the photo-active chemical agent and present in said blood fraction, are not in a position to interact with healthy intact lymphocytes circulating with the blood because, firstly, to provide for said therapeutic effect, the major part (up to 75%) of the immunocompetent cells (lymphocytes) available in the blood supply system of the patient must be exposed to radiation, and, secondly, the presence of other cellular elements in the blood, primarily erythrocytes, hinders direct contact between immunogenic photo-adducts and healthy cells. As regard the main immune response initiated by the emergence in the organism of changed antigenic structures as a result of photo adducts being introduced into the blood supply system, it is mainly localized within the spleen. But even the spleen receives but a limited portion of these immunogenic photo-adducts. This is due to the fact that a substantial part of these immunoreagents to be found in the blood gets attached to the surfaces of macrophages, and since the entire blood passes through the liver where a large number of macrophages is to be found, the major part of the immunogenic adducts introduced into the blood becomes concentrated in the liver, as well as in the kidneys and lungs, and only the remaining portion (up to 10% of the total quantity) falls to the share of the spleen.

This is what reduces the therapeutic effect provided by exposure to radiation.

SUMMARY OF THE INVENTION

It is an object of the present invention to enhance the therapeutic effect upon a living organism with a lymphatic system.

Another object of the invention is to provide a method for producing a therapeutic effect upon the organism, such that would ensure more active suppression of pathologic cells and their proliferation.

A further object of the invention is to provide a method for producing a therapeutic effect upon the organism, such as would ensure a more powerful immune response by the organism to the introduction therein of immunogenic photo-adducts.

In accordance with the invention, the method of producing a therapeutic effect upon a living organism provides for obtaining from said organism a biological fluid, wherein lymphocytes make the predominant cellular constituent, and for exposing said fluid to ultraviolet radiation. Prior to irradiation, said biological fluid has a fluid-soluble photo-active chemical agent added to it. On completion of the irradiation, the biological fluid is returned to the lymphatic system of the organism.

In this method of producing a therapeutic effect upon the organism, the immunogenic photo-adducts formed by exposure to ultraviolet radiation with the participation of constituents of the treated fluid and molecules of the photo-active chemical agent, will find their way into a medium with a significant concentration of healthy intact lymphocytes and, in consequence thereof, they will be enabled to actively interact therewith. This will lead immediately to initiation of a response at the level of the population of lymph-circulated healthy immunocompetent cells. As a result, there occurs a much more effective suppression of pathologic lymphocytes circulating in the organism than provided in the prototype, leading to a considerably enhanced therapeutic effect. Moreover, while moving with the lymph into the thoracic duct and further on into the blood, the photo-adducts pass through a whole series of lymphonodi which form, in response to such a stimulus, a generalized immune response involving the entire lymphoid system. This also contributes to more active suppression of pathologic cells, and the efficiency of the therapeutic effect upon the organism is thereby enhanced.

For biological fluids, wherein lymphocytes prevail as a cellular constituent, use may be made of lymph directly originating from the lymphatic system of a patient or of a lymph fraction enriched with lymphocytes or of a blood fraction enriched with lymphocytes.

In another embodiment of the invention, irradiation is effected directly in one of the vessels of the lymphatic system of a living organism.

A photo-active chemical agent to be used may be: (1) some one of the active furocoumarins as such or a combination of furocoumarins, also, ethylene blue, pyrene, cholesteryloleate, protoporphyrin, porphyrin, acridine, fluoroscein, rodamine, 16-diazocortisone, ethidium, a transition metal complex of bleomycin, a transition metal complex of deglycobleomycin, or an organoplatinum complexes; (2) a polypeptide selected from the group consisting of interleukin, transferrin, thyopoietin, insulin, antibodies, and monoclonal antibodies, and covalently linked with a photo-active cytotoxic agent; or (3) a liposoma linked with a polypeptide which comprises a photo-active cytotoxic chemical agent selected from the group consisting of furocoumarins, pyrene, cholesteryloleate, protoporphyrin, porphyrin, acridine, fluoroscein, rodamine, 16-diazocortisone, ethidium, a transition metal complex of bleomycin, a transition metal complex of deglycobleomycin, or organoplatinum complexes.

DETAILED DESCRIPTION OF THE INVENTION

The inventive therapeutic effect is realized as follows. A biological fluid, with lymphocytes as the main cellular component, is withdrawn from the organism. To this end, blood may be drawn from a patient, and centrifuged in a conventional manner to separate a fraction containing lymphocytes as the main constituent, with lymphocyte-free fractions to be returned to the blood supply system of the patient. This done, the blood fraction rich in lymphocytes is placed in a cuvette, and a photo-active chemical agent is added thereto. As disclosed in U.S. Pat. No. 4,613,322, this agent may be selected from: (1) some one of the active furocoumarins, or a combination of furocoumarins, methyl blue, pyrene, cholesteryloleate, acridine, porphyrin and protoporphyrin, fluorescein, rodamine, 16-diazocortisone, ethidium, transition metal complexes of bleomycin, transition metal complexes of deglycobleomycin, organoplatinum complexes; (2) a polypeptide selected from the group consisting of interleukin, transferrin, thymopoietin, insulin, antibodies, and monoclonal antibodies, and covalently linked with a photo-active cytotoxic agent; or (3) a liposoma linked with a polypeptide which comprises a photo active cytotoxic chemical agent selected from the group consisting of furocoumarins, pyrene, cholesteryloleate, protoporphyrin, porphyrin, acridine, fluorescein, rodamine, 16-diazocortisone, ethidium, a transition metal complex of bleomycin, a transition metal complex of deglycobleomycin, or organoplatinum complexes. Introduction of an agent into the biological fluid may be also provided by way of administering of directly onto the organism of a patient prior to blood withdrawal.

Following the addition of a photo-active chemical agent to the lymphocyte-rich biological fluid and a short period of mixing, the agent is adsorbed on the surfaces of cellular membranes and cellular elements and also on DNA sections, assuming that the agent is capable of penetrating into the cell's nucleus and has affinity towards DNA.

Then the biological fluid (blood fraction) in the cuvette is irradiated using ultraviolet light with wavelength of 200 to 800 nm, the wavelength being varied in relation to the photo active chemical agent employed. Mercury-vapour lamps, xenon lamps, or lasers may be used for purposes of irradiation.

In the case of agents intercalating in darkness between pairs of DNA pyrimidines, the radiation effect results in irreversible DNA degradation or in covalent linkage being formed between pyrimidines from complementary DNA chains, with the photo-active chemical agent participating therein.

As a result, stable complexes are formed, with clearly pronounced modified stable antigenic properties. The use of known natural compounds and pharmaceuticals linked with photo-active chemical groups, antibodies, natural polypeptides, including interleukin, transferrin, etc., cortisone, and the like, for which there are appropriate receptor sites on cellular membranes, leads to a more powerful manifestation of their biological activity aimed at direct degradation or suppression of the functional end metabolic activity of the target cells, the result being formation in the irradiated fluid or photo-altered non-viable cells and fragments thereof which are capable, when introduced into the lymphatic system, of causing a reaction from the healthy constituents of the lymphoid tissue. In consequence of the fact that the metabolic processes characteristic of a living cell are considerably more active in pathologic cells than in healthy ones, it is pathologic cells that are subjected primarily to degradation and loss of functional activity. In the event of the biological fluid being exposed to ultraviolet radiation in the presence of a photo-active chemical agent having the properties of a photosensitizer, such as a psoralen, and in a medium with an insignificant oxygen content (specifically, when the biological fluid sample is slightly vacuumized prior to exposure), the photochemical reactions in the fluid become oriented towards formation of diadducts of psoralen and DNA filament and, alongside with inhibition of the division processes of the treated cells. Formation of artificial division homogeneous structures capable of provoking in healthy immunocompetent cells a strong reaction against said homogeneous antigenic structures.

Should there be need for initiating a be polyvalent immune response from the organism, the biological fluid may be conveniently treated in the presence of an elevated oxygen content so that the oxygen-dependent reactions of the photo-active chemical agents in the biological substrate might be intensified. This can be easily achieved by irradiating the fluid, with 8-methoxy psoralen or some other photosensitizer dissolved therein, in a vessel where oxygen is supplied under pressure. With this arrangement. reactions of a radical nature occuring in the fluid will cause degradation of many cellular structures and modification of the cellular surfaces of a considerable number of immunocompetent cells, as well as formation of numerous cellular fragments covalently linked with photo-active agent molecules and possessing immunogenic properties.

Next, the treated blood fraction is introduced into the lymphatic system. To this end, a lymphatic vessel is catheterized in a conventional manner. It is convenient to choose for the purpose one of the lower extremities.

A clearly pronounced immune response is to be observed when the treated fluid is introduced into the lymphatic system. The possibility of contact between the immunogenic photo-adducts and certain groups of cells of the lymphoid organs depends on the anatomic position of these cells. Where the immunogenic photo-adduct is introduced endolymphatically (or into the fatty surrounding lymphonodi or into lymphonodi, which is technically more difficult). this immunoreagent is delivered with the lymph to the lymphonodi responsible for draining of a given area, where it interacts with the macrophages of the medullar region and the dendritic cells of the lymphoid follicles and passes nearly in its entirety through the regional lymphatic nodi. This causes a powerful generalized immune response from the entire system. There are no constituents in the lymph that could screen the healthy intact lymphocytes present therein from interaction with the immunogenic photo-adduct, and for this reason direct interaction is possible between the healthy intact lymphocytes and the immunogenic photo-adducts with the result that a reaction is initiated on the part of the healthy intact lymphocytes, aimed at suppression of pathologic cells. An essential therapeutic effect can be obtained here, using but slight quantities of the immunoreagent.

Considering the fact that in malignant lymphoproliferative diseases and in auto-immune diseases the pathologic cells are considerably more numerous than healthy ones, they can form - on their return to the organism after said treatment and formation of immunogenic photo-adducts- that critical mass of immunoreagents which causes the formation of an immune response by the system. When introducing the treated cells into the organism endolymphatically, there is a possibility of direct interaction between immunogenic photo-adducts and healthy immunocompetent cells, e.g. based on anti-idiotypic reactions. Besides, it is quite possible that a strong immune response may be associated with a mixed lymphocyte culture reaction being initiated right in the lymphatic system, more particularly when the cell treated has been performed at an elevated oxygen concentration.

We have discovered in our in vitro experiments that co-cultivation of intact lymphocytes and autologic lymphocytes irradiated in the presence of a photo-active chemical agent leads to higher activity in the DNA synthesis in the cells of the culture as a whole. It may be assumed in this connection that ultraviolet irradiation leads to changes in the histocompatibility antigens in the HLAF region while the subsequent re-infusion of irradiated cells into the organism initiates mixed culture reactions. The biological effect at the organism level may thus be associated with the mixed culture reaction being induced throughout the circulating lymph and manifested as blast transformation of T-lymphocytes and formation of cytotoxic T-lymphocytes which may have a toxic effect upon target lymphocytes.

Said biological fluid may be lymph enriched with lymphocytes. To be used as such, lymph is withdrawn from a patient, centrifuged, and a fraction enriched with lymphocytes is isolated. Although lymph withdrawal is a more complicated procedure than blood withdrawal, the vessels of the lymphatic system being narrower, yet a much lower quantity of fluid is to be withdrawn and treated in this case in order to obtain a clearly pronounced immune response.

Lymph can also be used as a biological fluid as such, without being fractionated.

As a matter of principle, cerebro-spinal fluid which contains immunocompetent cells may also be used as a biological fluid, but its use is less preferable, considering the risk of a trauma to the patient incident to its withdrawal, as well as the relatively low concentration (up to 10%) of immunocompetent cells therein.

For forced saturated of the biological fluid with oxygen before irradiation, the biological fluid is placed into a container capable of withstanding a pressure of 2 to 3 atm. This container should either have one of the walls made quartz and allow of an extended radiation source to be arranged above it or have a fibre-optic light guide secured in one of the walls and connected optically via a focusing system with a radiation source. Connected to the container via a connecting hose is a compressed oxygen vessel equipped with a reducing valve.

For pre-irradiation vacuumization, the biological fluid is placed into a container which also has one of the walls made of quartz or a fibre-optic light guide in one of the walls. Connected to this container via a connecting hose is a pump placed over a special pipe stub provided on the container.

In accordance with another embodiment of the invention, irradiation is effected endolymphatically. A thin catheter is introduced into a lymphatic vessel, and a fibre optic light guide is inserted down the entire depth of the catheter, the light guide being optically connected via a lens system to a point ultraviolet radiation sirocco. A photo-active chemical agent is either administered to the patient per os 4 to 8 hours before the treatment or supplied endolymphatically at regular intervals in small portions in the course of treatment. In intracorporeal lymph treatment, some of the known means may conveniently be used to accelerate lymph flow through the vasal channel. The processes incident to intracorporeal lymph treatment are similar to these occuring in extracorporeal treatment. Intracorporeal irradiation will greatly reduce the risk of traumatism involved in the procedure and provides better opportunities for interaction between immunogenic photo-adducts and healthy cells. Also, with this arrangement, immunogenic photo-adducts are supplied to the lymphatic system at a constant rate, i.e. the load on the lymphonodi is distributed more informly, and this provides for more stable functioning of the immune system.

Puncturing points in lymphatic vessels may conveniently be chosen on a lower extremity because, considering the anatomic structure of the lymphatic system, an immunogenic photo-adduct fragment introduced thereinto will inevitably pass-before entering the blood supply system—through the entire system of regional lymphonodi, of which there will be quite a number to be encountered in its path, with the result that a powerful immune response will be provoked and the probability and period of interaction of healthy cells therewith will be considerably increased to further enhance the immune response.

The proposed method may be illustrated with the following specific examples of its implementation.

EXAMPLE 1

A cow, breed black-mottled, diagnosed as having acute lymphoid leukosis accompanied with a considerable increase in the total number of leucocytes in the blood—to 35,000 per microliter.

A syringe of 300 ml capacity was used to withdraw 250 ml of blood from the cow's jugular vein. The withdrawn blood was established with heparin, 15 units per milliliter. Then it was fractionated by centrifuging for 20 minutes at a centrifuge rotor speed of 2000 rev/min. The fraction enriched with lymphocytes, in the amount of 25 ml. was collected in a sterile flask. The remaining plasma and erythrocyte mass were mixed together and introduced back into the cow's blood supply system by means of a syringe through the original puncture point. The blood withdrawal and separation procedure was repeated 7 more times, so that 200 ml of lymphocyte-in-plasma suspension was collected in the flask in the long run.

Then 40 mg of psoberane (preparation comprising a mixture of 8-methoxy psoralen and bergaptene) was added to the suspension-containing vessel, and the contents were mixed in a special shaker. Next, the suspension was irradiated while passed through a cuvette sized 140×25×1 mm and providing a luminous energy intensity of 2 mw/cm$^2$ in the cuvette plane. The suspension flow rate through the cuvette was 20 ml/min. Nearly 90% of the luminous energy intensity in the cuvette plane was provided by ultraviolet radiation with a maximum near 350 nm.

Then a lymphatic vessel in a rear extremity was drained, and a catheter installed, enrich catheter was used to introduce the irradiated suspension at the rate of 1,5 ml per minute.

The same procedure was repeated 5 more times at intervals of 10 to 15 days. Already after the third procedure the animal showed an improved clinical picture. On completion of the course of treatment the concentration of leucocytes in the blood was 800 per microliter. This value continued practically unchanged an observation period of 11 months.

EXAMPLE 2

Patient K., male, age 16, delivered with a diagnosis of acute T-cell leukosis in the exacerbation phase. By the time of delivery the patient has suffered from the disease for 2 years, during which period he had undergone 3 courses of treatment based on conventional chemotherapy. The concentration of blast cells in the blood was up to 30%.

Five hours before the commencement of the procedure, the patient was administered intravenously a solution containing 30 mg of 8-methoxy psoralene. The lymphatic duct was drained in the left leg, in the groin area, and a catheter was installed. A fibre-optic light guide was inserted throughout the length of the catheter, having a high transmission coefficient in the UVA region and connected optically via a focusing lens system to a point source based on the use of a xenon lamp and providing a luminous energy intensity at outlet from the light guide of 1 mW in the UVA region (fibre optic conductor diameter being 0.8 mm). The radiation time per procedure was up to 120 minutes. The intervals between procedures were 7 to 14 days. A total of 6 procedures were carried out. For several days after each procedure the patient received up to 200 mg of allopurinol daily.

On completion of the course of treatment, no blast cells were to be found in the peripheral blood. The concentration of various forms of leucocytes was typical for patient suffering from leukosis in the remission phase.

EXAMPLE 3

Patient T., male, age 39, delivered with a diagnosis of bronchial asthma in the abating exacerbation phase and respiratory deficiency.

Four hours before the commencement of the procedures, the patient was administered per os 30 mg of beroxane (preparation comprising a mixture of 8-methoxy psoralen and bergaptene). The lymphatic duct in the leg in the groin area at left was catheterised. A light guide connected to an U.V. source was introduced throughout the length of the catheter. The luminous energy intensity at outlet from the light guide was 2 mW (the diameter of the fibre optic light conductor being 0.8 mm). The irradiation time per procedure was 40 to 60 minutes. The procedure were carried out at intervals of 10 days. A total of 5 procedures were carried out.

Already after the first procedure, rhinocleisis and rhinorrhea were no longer to be observed. Asphyxia fits became much less frequent, and the quantity of secreted sputum was decreased. On completion of the treatment, stable remission was to be observed, as well as improved endurance of physical strains.

We claim is:

1. A method of producing a therapeutic effect upon a living organism endowed with a lymphatic system, comprising the steps of:

withdrawing from said organism a biological fluid, wherein lymphocytes prevail as the cellular constituent;

introducing into said biological fluid a photo-active chemical agent soluble in said fluid, having a specific affinity for the receptor sites in or on the constituents of said fluid capable of being activated by ultraviolet radiation, and capable, when activated by said ultraviolet radiation, of forming photo-adducts with receptor sites of the constituents of the lymphocytes-rich fluid, thereby ensuring chemical linkages between said photo-active chemical agent and said receptor sites;

wherein said biological fluid is force saturated with oxygen prior to being irradiated by ultraviolet light, or wherein said biological fluid is vacuumized prior to being irradiated by ultraviolet, or wherein said biological fluid is force saturated with oxygen and is vacuumized prior to being irradiated by ultraviolet;

irradiating said biological fluid, with said photo-active chemical agent introduced thereinto, by ultraviolet light; and introducing said biological fluid after said irradiation directly back into said lymphatic system.

2. A method as defined in claim 1, wherein said biological fluid is blood;

and said method further comprises isolating from said blood a fraction enriched with lymphocytes; and using said blood fraction enriched with lymphocytes as said biological fluid.

3. A method as defined in claim 1, wherein said photo-active chemical agent is a member selected from the group consisting of 8-methoxy psoralen, bergaptene, isopsoralen, isopimpinellin, pyrene cholesteryloleate, acridine, porphyrin, protoporphyrin, fluorescein, rodamine, 16-diazocortisone, ethidium, a transition metal complex of bleomycin, a transition metal complex of deglycobleomycin, an organoplatinum complex, and mixtures thereof.

4. A method as defined in claim 1, wherein said biological fluid is lymph from the lymphatic system of said organism.

5. A method as defined in claim 4, further comprising isolating from said lymph a fraction enriched with lymphocytes and using said fraction enriched with lymphocytes as said biological fluid.

6. A method as defined in claim 1, wherein said photo-active chemical agent is a polypeptide selected from the group consisting of interleukin, transferrin, thympoietin, insulin, antibodies, and monoclonal antibodies, said polypeptide covalently linked with a photo-active cytotoxic agent selected from the group consisting of 8-methoxy psoralen, bergaptene, isopsoralen, isopimpinellin, pyrene cholesteryloleate, acridine, porphyrin, protoporphyrin, fluorescein, rodamine, 16-diazocortisone, ethidium, a transition metal complex of bleomycin, a transition metal complex of deglycobleomycin, an organoplatinum complex, and mixtures thereof.

7. A method as defined in claim 6, wherein said photo-active chemical agent is said polypeptide linked with a liposoma comprising said photo-active cytotoxic agent.

8. A method of producing a therapeutic effect upon a living organism endowed with a lymphatic system and lymph circulating therein, comprising:

introduction of a photo-active chemical agent into said organism and subsequent intracorporeal irradiation by ultraviolet light of said lymph circulating through the lymphatic system;

wherein said lymph irradiation is effected by using a fiber optic light guide, of which the free end is introduced into one of the vessels of said lymphatic system.

9. A method as defined in claim 8, wherein said vessel of the lymphatic system is located in one of the lower extremities of said organism.

10. A method as defined in claim 8, wherein said photo-active chemical agent is selected from the group consisting of 8-methoxy psoralen, bergaptene, isopsoralen, isopimpinellin, pyrene cholesteryloleate, acridine, porphyrin, protoporphyrin, fluorescein, rodamine, 16-diazocortisone, ethidium, a transition metal complex of bleomycin, a transition metal complex of deglycobleomycin, an organoplatinum complex, and mixtures thereof.

11. A method as defined in claim 8, wherein said photo-active chemical agent is a polypeptide selected from the group consisting of interleukin, transferrin, thympoietin, insulin, antibodies, and monoclonal antibodies, said polypeptide covalently linked with a photo active cytotoxic agent selected from the group consisting of 8-methoxy psoralen, bergaptene, isopsoralen, isopimpinellin, pyrene cholesteryloleate, acridine, porphyrin, protoporphyrin, fluorescein, rodamine, 16-diazocortisone, ethidium, a transition metal complex of bleomycin, a transition metal complex of deglycobleomycin, an organoplatinum complex, and mixtures thereof.

12. A method as defined in claim 11, wherein said photo-active chemical agent is said polypeptide linked with a liposoma comprising said photo-active cytotoxic agent.

13. A method of producing a therapeutic effect upon a living organism endowed with a lymphatic system, comprising:

withdrawing from said organism a biological fluid wherein lymphocytes prevail as the cellular constituents;

introducing into said biological fluid a photo-active chemical agent soluble in said fluid and having a specific affinity for the receptor sites in or on the constituents of said fluid and being capable of being activated by ultraviolet radiation, and capable, when activated by said ultraviolet radiation, of forming photo-adducts with receptor sites of the constituents of said fluid, thereby ensuring chemical linkages between said photo-active chemical agent and said receptor sites;

irradiating said biological fluid, with said photo-active chemical agent introduced thereinto, by ultraviolet light; and introducing said biological fluid after said irradiation back into said lymphatic system;

said biological fluid being force saturated with oxygen prior to being irradiated by ultraviolet light.

14. A method of producing a therapeutic effect upon a living organism endowed with a lymphatic system, comprising:

withdrawing from said organism a biological fluid wherein lymphocytes prevail as the cellular constituents;

introducing into said biological fluid a photo-active chemical agent soluble in said fluid and having a specific affinity for the receptor sites in or on the constituents of said fluid and being capable of being activated by ultraviolet radiation, and capable, when activated by said ultraviolet radiation, of forming photo-adducts with receptor sites of the constituents of said fluid, thereby ensuring chemical linkages between said photo-active chemical agent and said receptor sites;

irradiating said biological fluid, with said photo-active chemical agent introduced thereinto, by ultraviolet light; and introducing said biological fluid after said irradiation back into said lymphatic system;

said biological fluid being vacuumized prior to being irradiated by ultraviolet light.

* * * * *

UNITED STATES PATENT AND TRADEMARK OFFICE
CERTIFICATE OF CORRECTION

PATENT NO. : 5,571,082
DATED : November 5, 1996
INVENTOR(S) : Alexei B. Bashkirov It is certified that error appears in the above-identified patent and that said Letters Patent is hereby corrected as shown below:

On the title page, under item [19], and item [76], change "Bashikirov" to --Bashkirov--.

Signed and Sealed this

First Day of April, 1997

*Attest:*

BRUCE LEHMAN

*Attesting Officer*  Commissioner of Patents and Trademarks